United States Patent [19]

Koal

[11] Patent Number: 4,499,394

[45] Date of Patent: Feb. 12, 1985

[54] POLYMER PIEZOELECTRIC SENSOR OF ANIMAL FOOT PRESSURE

[76] Inventor: Jan G. Koal, NE. 820 California St., Pullman, Wash. 99163

[21] Appl. No.: 544,227

[22] Filed: Oct. 21, 1983

[51] Int. Cl.³ .................................................. H01L 41/08
[52] U.S. Cl. ...................................... 310/330; 310/319; 310/338; 310/340; 310/800; 310/358
[58] Field of Search ............... 310/330, 338, 800, 358, 310/319

[56] References Cited

U.S. PATENT DOCUMENTS

| | | | |
|---|---|---|---|
| 3,239,696 | 3/1966 | Burkhalter | 310/338 X |
| 3,323,367 | 6/1977 | Searle . | |
| 3,604,958 | 9/1971 | Palini | 310/330 X |
| 3,750,127 | 7/1973 | Ayers et al. | 310/800 X |
| 3,798,474 | 3/1974 | Cassand et al. | 310/800 X |
| 4,054,808 | 10/1977 | Tanaka | 310/330 X |
| 4,216,403 | 8/1980 | Krempl et al. | 310/800 |
| 4,304,126 | 12/1981 | Yelke | 310/800 X |
| 4,328,441 | 5/1982 | Kroeger, Jr. et al. . | |

FOREIGN PATENT DOCUMENTS

| | | |
|---|---|---|
| 2653266 | 6/1977 | Fed. Rep. of Germany . |
| 2832943 | 2/1978 | Fed. Rep. of Germany . |
| 2497345 | 7/1982 | France ............................. 310/338 |
| WO81/02223 | 8/1981 | PCT Int'l Appl. . |

*Primary Examiner*—Mark O. Budd
*Attorney, Agent, or Firm*—Keith S. Bergman

[57] ABSTRACT

A sensor structure for attachment to the foot of an animal to continuously measure the pressure of the foot against a reactive surface. The sensor structure provides a small flat particularly configured piece of piezoelectric plastic, encapsulated to protect it and interconnected electrically with telemetry and analyzing apparatus. Plural sensors may be used in various parts of a foot to determine local pressures. The sensed pressure may be recorded and annunciated by various known means to aid analysis of foot and limb activity and general animal physiology.

2 Claims, 8 Drawing Figures

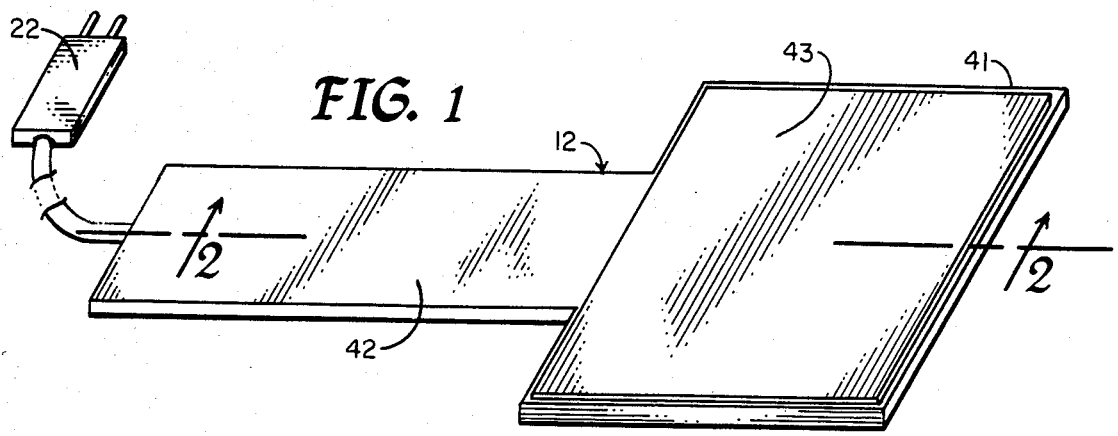
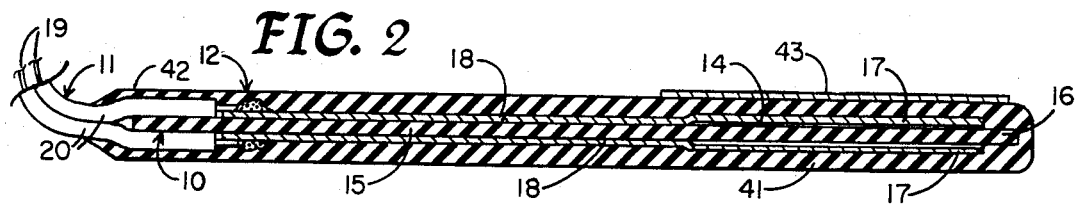
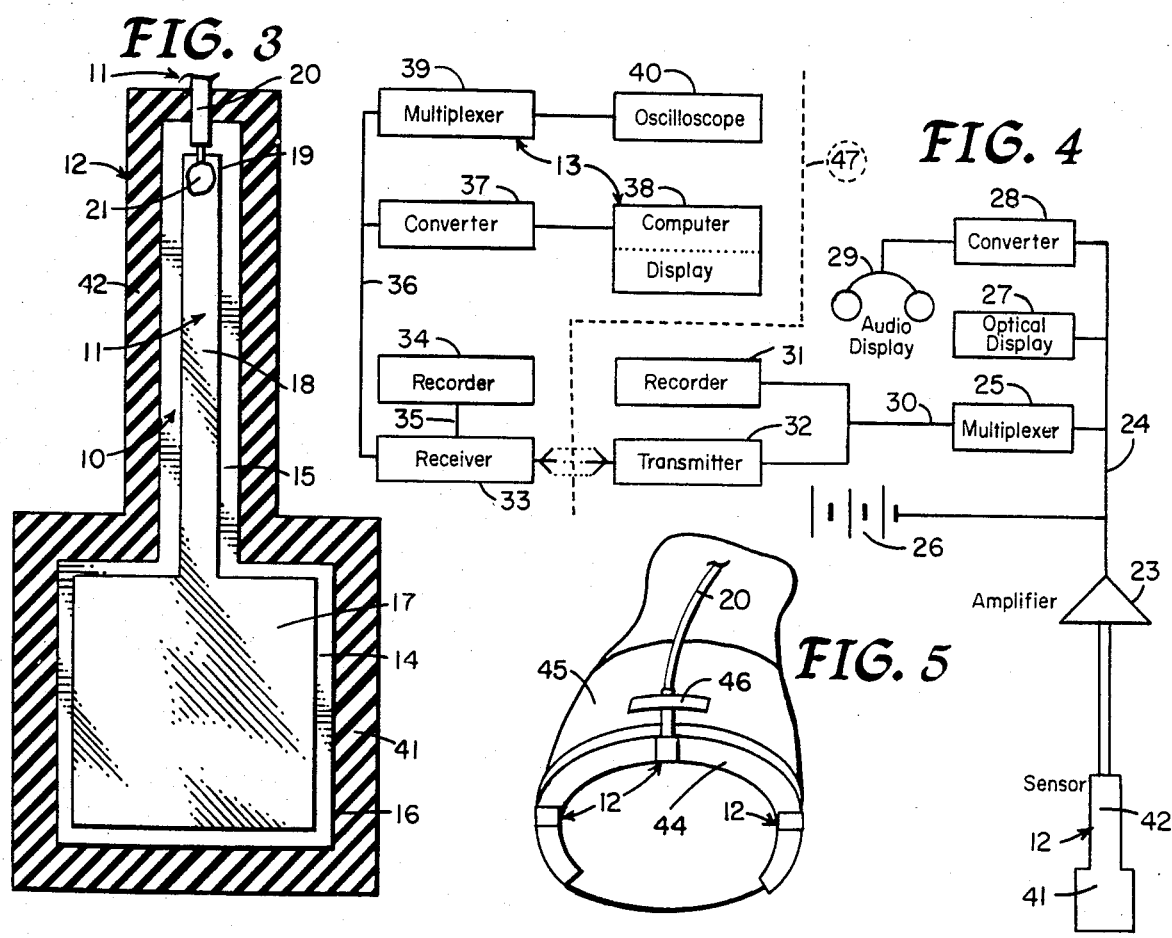

ered and particularly susceptible to impact and shock damage. This made such devices difficult to place in a sensory position, so that the results produced would be accurate and required quite complex structures to be associated with such devices to assure their durability and accurate responsiveness. My instant invention seeks to alleviate these problems by providing a relatively small piezoelectric device of low cost and substantial durability to sense pressures on an animal's foot in an instantaneous fashion with extreme accuracy and great reliability.

POLYMER PIEZOELECTRIC SENSOR OF ANIMAL FOOT PRESSURE

BACKGROUND OF INVENTION

1. Related Applications

There are no applications related hereto heretofore filed in this or any foreign country.

2. Field of Invention

My invention relates generally to piezoelectric pressure sensors and more particularly to such a device to continuously sense the pressure of an animal foot against a reactive supporting surface, especially during locomotive activities.

3. Description of Prior Art

In dealing with the physiology of running of various animals, even including man, it is oftentimes desirable or necessary to sense the time of contact of the animal's foot or portions of it on an underlying supporting surface and also to sense the pressure between the various parts of that foot and the supporting surface. These physiological parameters may be used to indicate various systemic deficiencies and anatomical problems, especially in the lower animals, as well as to study and explain the locomotive process itself. The determination of these parameters is somewhat of a problem in the case of animals below the evolutionary standard of man because of lack of rational communication, and yet this determination is even more important in such animals as they often cannot indicate the existence of deficiencies or problems by any particular indicative reaction. Oftentimes, even in man, systemic problems may exist and may not be timely sensed, especially in their earlier stages.

This situation has long been recognized, at least since Marey's studies of the physiology of running horses in the middle 1800's. In general, however, the primary thing that has heretofore been sensed has been the relative motion of an animal's legs as oriented in time and this sensing has been accomplished largely by cinematography of one sort or another. Obviously cinematographic methods of sensing animal motion do not determine or measure the pressure of the animal's foot upon an underlying reactive surface, and particularly do not demonstrate any differential pressures over various parts of the foot.

It has heretofore become known to sense the pressure of an animal's foot and its various parts upon a supporting surface, both absolutely and differentially during locomotion. Heretofore, however, such pressure sensation has been accomplished by some pneumatic or hydraulic device and the measurements produced have generally been more qualitative than quantitative and used largely to determine the time sequence of pressure contact of a foot in relation to the time of contact of another foot or other feet. The hydraulic and pneumatic methods of measurement have generally not been particularly accurate either in time or pressure measurement because of the compressability of the measuring medium, in the case of pneumatic devices and because of the relatively slow response time and system resistivity in the case of hydraulic instruments. Generally neither the known pneumatic nor hydraulic devices have had sufficient accuracy to distinguish between varying pressures on various parts of an animal's foot and because of this have not been used to so do.

Heretofore electronic sensing of animal foot pressure on a reactive surface during locomotion has not been too feasible, largely because the devices in common use for so doing—piezoelectric crystals or ceramic devices—were relatively large, delicate and particularly susceptible to impact and shock damage. This made such devices difficult to place in a sensory position, so that the results produced would be accurate and required quite complex structures to be associated with such devices to assure their durability and accurate responsiveness. My instant invention seeks to alleviate these problems by providing a relatively small piezoelectric device of low cost and substantial durability to sense pressures on an animal's foot in an instantaneous fashion with extreme accuracy and great reliability.

My invention differs from the prior art by providing a sensing device formed with a plastic piezoelectric sensor having a relatively small areal extent, relative thinness and encapsulation with a metallic shield on the exposed surface to provide substantial durability. The sensing device is small enough that a plurality of them may be positioned on an animal foot, such as the hoof of a horse, to determine pressures simultaneously at a plurality of locations. The sensors may be either temporarily or permanently attached to an animal foot or shoe by adhesion or other mechanical means without in any way changing, damaging or modifying the foot or shoe to which they are attached. The sensor may be quite conveniently incorporated within a structure carried by the foot such as within a human shoe sole or between a metallic shoe and the hoof of a horse. A resilient backing is disclosed to allow sensor positioning over an indentation such as in a horseshoe. The plastic sheet material that constitutes my sensor is easily formed and fabricated, has great reliability and accuracy and provides substantial durability and reliability when properly configured and encapsulated.

The output of one or a plurality of sensors may be analyzed by associating apparatus carried by an animal being sensed or may be amplified and transmitted by ordinary telemetry devices at a distance from the animal. The signal may be recorded, either on or at a distance from the animal, in some physical form and thereafter analyzed to give relative times of various foot actions and to accurately measure pressures upon small areas of a foot. My invention, in providing such structure and functions is distinguished from the prior art individually and in any combination, as hereinafter more particularly set forth.

SUMMARY OF INVENTION

My invention in general provides a sensor having electrical circuitry to interconnect it with signal transmitting and analyzing apparatus, the sensor and connecting circuitry, at least, being encapsulated in a protective casement. The sensor is formed of sheet-like, plastic type piezoelectric material having opposed sensing surfaces of some areal extent. The opposed sensing surfaces of the sensor are each interconnected by metallic foil with electrical circuitry to communicate a signal generated by the sensor to amplifying telemetry and analyzing apparatus, the latter of which may be at a distance from the subject animal whose feet are being sensed. The encapsulated sensing device is positionally maintained by physical attachment, normally by adhesion, and its exposed external surface may be protected against physical injury by a thin, semi-rigid plate. The whole sensor is relatively small and generally semi-rigid.

In creating such a device it is:

A principal object of my invention to provide an electronic pressure sensor that may be positioned on the lower surface of an animal foot to accurately, instantaneously and continuously determine the pressure between a relatively small area of that foot and a reactive surface.

A further object of my invention to provide such a device that by reason of its nature and encapsulation has substantial reliability and durability, both of which may be enhanced by an additional rigid protective covering on the surface of the encapsulating material.

A further object of my invention to provide such a device that may be positioned on an animal foot to sense pressures thereagainst or may be placed on or in a shoe structure to sense pressures on the shoe, between the animal's foot and a shoe or between a shoe and a reactive surface.

A further object of my invention to provide such a device that is of such small size that a plurality of sensors may be positionally maintained on a foot or shoe to simultaneously determine pressures on different parts thereof.

A still further object of my invention to provide such a device that has associated, animal carried, circuitry for telemetry and data transmittal to a distant point where the data may be analyzed and recorded.

A still further object of my invention to provide such a device that is of new and novel design, of rugged and durable nature, of simple and economic manufacture and one otherwise well suited to the uses and purposes for which it is intended.

Other and further objects of my invention will appear from the following specification and accompanying drawings which form a part hereof. In carrying out the objects of my invention, however, it is to be understood that its essential features are susceptible of change in design, and structural arrangement with only one preferred and practical embodiment being illustrated in the accompanying drawings, as is required.

BRIEF DESCRIPTION OF DRAWINGS

In the accompanying drawings which form a part hereof and wherein like numbers of reference refer to similar parts throughout:

FIG. 1 is an isometric surface view of a typical sensing device of my invention.

FIG. 2 is an elongate, cross-sectional view of the sensing device of FIG. 1, taken on the line 2—2 thereon in the direction indicated by the arrows, to show the internal structure of the device.

FIG. 3 is a plan view of the sensor of FIG. 1 with the top portion of the casement removed to show internal structure.

FIG. 4 is a diagrammatic representation of my sensor with associated telemetry and analyzing apparatus.

FIG. 5 is a partial isometric view, looking upwardly, at a horse's hoof showing the placement of my sensors on the undersurface of a shoe carried by the hoof.

DESCRIPTION OF THE PREFERRED EMBODIMENT

Figure 6:
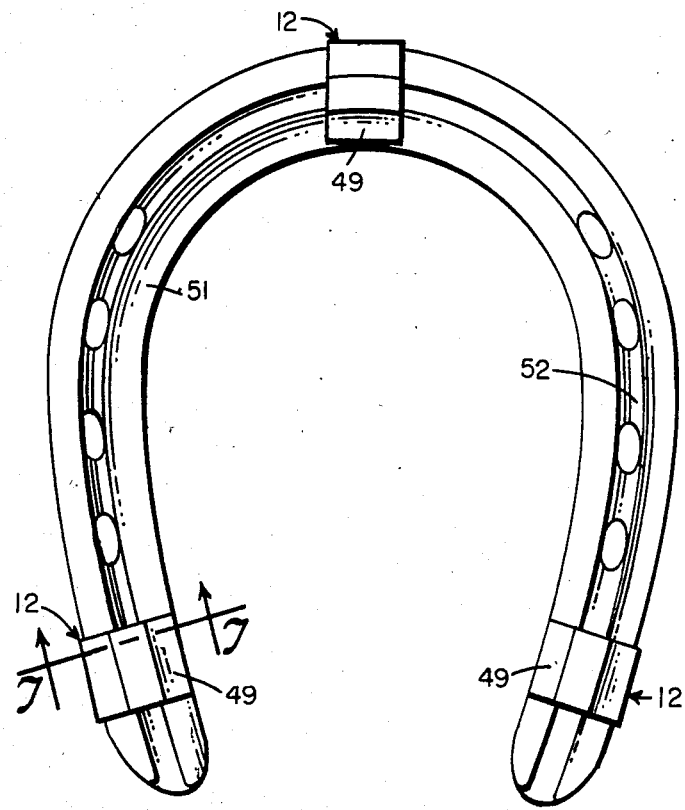
FIG. 6 is a view of the bottom of a typical horseshoe used for racing with my sensing devices positioned over the groove therein by use of a resilient backing block.
Figure 7:
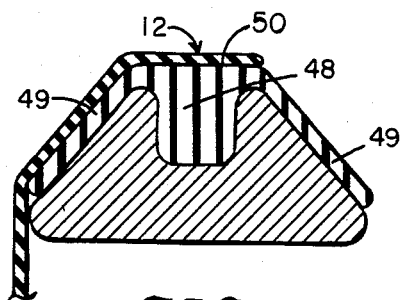
FIG. 7 is a vertical, cross-sectional view through a sensor and backing block of FIG. 6, taken on the line 7—7 thereon in the direction indicated by the arrows.
Figure 8:
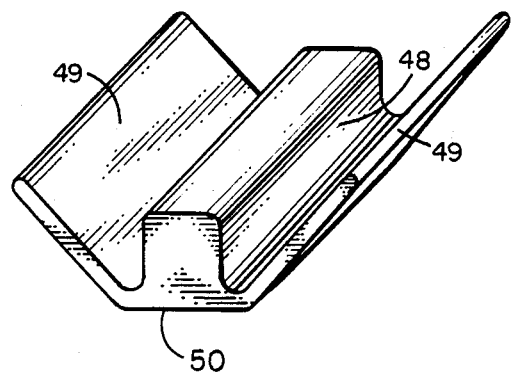
FIG. 8 is an isometric view of the normally upper surface of a typical resilient backing block.

My invention comprises generally piezoelectric sensor 10 enclosed in casement 12 and communicating by connecting circuitry 11 with telemetry and analyzing apparatus 13.

Piezoelectric sensor 10 is a sheet-like, pliable, polymeric piezoelectric film which is presently commercially available. I prefer the polyvinylidene fluoride type material manufactured by the Kynar Piezo Group of Penwalt Corporation, 900 First Avenue, King of Prussia, Pa., which is merchandised by that manufacturer under the tradename KYNAR. This particular type of material seems to produce higher piezoelectric values under similar parameters than other types of present day products, has good fidelity throughout a broad range of frequencies, high dielectric strength and resistance to moisture and is tough, flexible and light weight. Obviously other piezoelectric plastics of present day commerce would be operative with my invention, if not so well.

This type of piezoelectric plastic is commercially available in sheet form and may be readily cut to predetermined configuration by any means that would cut ordinary plastic film. I prefer to form my sensor element in the shape illustrated in FIG. 1, with larger sensing body 14 communicating with connecting tail 15. The preferred configuration is proportionately such as illustrated, but the illustration is approximately three times larger than the preferred size of my sensing unit for ordinary applications. Preferably the peripheral edges 16 of the sensor are smoothly cut to avoid the potentiality of future tearing or cracking. The absolute size and configuration of the sensor element are not critical to my invention as piezoelectric plastics will generally produce reactions in very small areas, but I have found that for accuracy and reliability there should be a reaction area that is of reasonably coherent shape and of approximately one quarter square inch area. Normally a single thickness of the material is sufficient for the purposes of my invention but if it be desired, to multiply the transducer response, plural sensors may be multiply interconnected either serially or in parallel and either electrically or physically.

Plastic piezoelectric sensors have a thin metallic film on the outer surface of both sides of the sheet material. Preferably this metallic film is left in place only upon the sensing area per se and is etched away from other areas of the film by known chemical or physical means. As shown in FIG. 1, the entire connecting tail and the peripheral border of the sensor body outside the foil connecting plate would all be etched so as to be inoperative in piezoelectric effect. This etching is not necessary for the functioning of the piezoelectric sensor but it is desirable to eliminate irregularities and electrical noise caused by imperfections in the plastic material, especially about the periphery of the sensor where such imperfections are most probable in occurrence.

Connecting circuitry 11 provides relatively thin, metallic foil connectors having a shape similar to but slightly smaller than the shape of the piezoelectric sensor. Each provides larger sensor connecting portion 17 and structurally integral elongate contact tail 18. This sensor element 17, 18 may be formed of many electrically conductive materials but I prefer a thin metallic foil of copper because not only of its desired electrical characteristics but also of its resilience and pliability.

Two such connector strips are required for a sensor to be operative, one positioned on each side of the piezoelectric sensor in the position substantially as illustrated in FIG. 3, with each connecting portion 17 adjacent one sensing surface. The adjacent surfaces of the sensor 14 and the foil connector 17 are adhered with some type of electrically conductive adhesive of present day commerce. I prefer electrically conductive epoxy or pressure sensitive foil for this purpose. Only a very thin film of adhesive should be used for adhesion of the elements to avoid undue reaction. Adjacent surfaces of connecting tail 15 and foil contact tail 18 are adhered with some type of known electrically non-conductive adhesive to prevent establishment of piezoelectric effects in this area.

A length of electric or conductive wire 19 of appropriate size and having peripheral insulation 20 is fastened to the outer end of each contact tail 18 of the metallic foil by soldering 21, or adhering with conductive adhesive, the exposed end of the wire to the foil, inwardly adjacent its outermost end as illustrated in FIGS. 2 and 3. These two wire conductors are generally interconnected by means of their insulation but each wire remains electrically independent to transmit electric current generated by the piezoelectric plastic upon proper stimulation. The wires are provided with connecting plug 22 in their end parts, some distance from the sensor, so that they may readily be releasably interconnected into various electrical circuitry. Normally I have found stranded copper wire wound from relatively fine strands of metal to be preferable for use with my invention, as opposed to solid metal wire, because the stranded wire is more pliable and has less potentiality of damaging either the sensor or the connecting metallic foil.

Casement 12 is provided to protect the sensor and the connecting circuitry proximately associated with it. The casement preferably has a shape similar to, though slightly larger than, the sensor with larger body portion and elongate tail portion 42 projecting therefrom. The casement is formed of some reasonably pliable, though, durable material, preferably such as one of the present day plastics—phenolic, neoprene or urethane plastics, especially if impregnated with re-enforcing fibers, are quite appropriate. Encasement may be accomplished by any of the common methods of present day plastic manufacturing arts such as molding, dipping, enveloping or the like. The casement may quite easily be formed from sheet plastic material by cutting the material to an appropriate shape, folding it to form a complete envelope and adhering it in place by some polymeric type adhesive established between the adjacent surfaces of the sensor, connector and casement.

Oftentimes portions of the outer surface of the encased sensor, especially its surface immediately over the sensing area, will be exposed to substantial physical forces, such as in the case of the exposed undersurface of a sensor positioned on a horse's hoof. To additionally protect this casement surface and ultimately the entire sensor, protective plate 43 normally formed of metal may be positioned upon the outer surface of the casement. Such a protective plate is normally structurally and positionally maintained by adhesion. This plate, if reasonably rigid, has a secondary advantage of serving as a pressure distributor to tend to equalize pressures upon the sensor therebeneath and thereby increase not only the reliability but also the sensitivity of that sensor.

It may be desirable to position my sensor over an indentation such as over the medial nail groove 52 of a typical racing type of horseshoe 51 as seen in FIG. 6 et seq. This may be readily accomplished by use of an appropriate configured semi-rigid backing block having body 48 to fit within nail groove 52 and similar lateral fastening wings 49 to present a flat lowermost surface 50 on which my sensor may be positioned. Such a backing block is formed of semi-rigid material such as hard rubber or plastic and positionally maintained by mechanical fastening, such as by adhesion. My sensor is positionally maintained thereon by mechanical fastening as aforedescribed.

Electrical sensing apparatus 13 and connecting circuitry 11 associated with my sensor to transmit signals at a distance from the point of generation and analyze those signals both quantitatively and qualitatively is well known in the electrical arts and is not therefore described in any detail. A typical system that might be used is shown in the diagrammatic representation of FIG. 4. Here it is seen that sensor 10 is electrically interconnected with amplifier 23, which preferably is of the high input impedance differential type. This amplifier is powered by battery 26 and is fed through line 24 to multiplier 25, optical display 27 and converter 28 which activates audio display 29. The output of multiplier 25 is passed in parallel through line 30 to recorder 31 and radio transmitter 32.

The output of radio transmitter 32 passes by aerial transmission at a distance to radio receiver 33 where it is received for further analysis. The signal passes through line 35 to recorder 34 where a permanent physical record is made and also through line 36 in parallel to converter 37 in series with computer and display 38 and to multiplexer 39 which outputs in series to oscilloscope 40 for optical display.

In normal practice is is usually desirable to have as little as possible of the analyzing equipment in immediate proximity to the sensor, so it generally is carried elsewhere on the animal that is being sensed. Normally only the apparatus to the right of dashed line 47 will be carried by the animal, though obviously other components might be so carried if desired. The apparatus to the left of dashed line 47 is located at a distance from the animal being measured. All of the animal carried components in modern day electrical practice may be quite small both in mass and bulk and generally cause no harmful burden to an animal.

Obviously other arrangements and types of telemetry and analyzing apparatus may be used with my invention and those set forth are set forth only as an example. It is quite possible that with my sensor a small amplifier and radio transmitter might be associated directly with it at the sensing location to transmit a signal at a distance before any modification or analysis of the sensed signal is had. Again, it is just as possible, especially in test environments, to directly wire the sensor on an animal being sensed to the ancillary electrical equipment whether such equipment be located at a distance or directly on the animal itself.

Having thusly described my invention, its operation can now be understood.

Firstly, one or more sensors are constructed according to the foregoing specifications and if for use on horses' feet as in the illustrated example, all are provided with protective plates on the exposed surface of the casement that is outwardly adjacent the sensing area.

A group of three sensors is shown attached to the bottom surface of a horse's foot in FIG. 5. Sensor body 41 of the casement is positioned flat against the under surface of flat bottomed horseshoe 44 and the connecting tail 42 of the device is bent upwardly to fit over the vertical surface of the shoe and against the outer surface of the horse's hoof 45. The sensor portion of the device may be positionally maintained by adhesion and the connecting tail may be maintained by direct adhesion or by use of adhesive tape 46 or similar releasable mechanical fasteners. Connecting wires 20 may be interconnected with telemetry and analyzing equipment 13 to receive and analyze the signals produced by the piezoelectric sensors responsive to forces thereon during motion of the horse's hoof being sensed. The signal produced by a sensor will vary functionally in voltage responsive to the amount of pressure impressed thereon. These functional relationships may be empirically determined and are known in the existing art.

The sensors generally and most conveniently may be established on the underside of an animal foot by means of direct adhesion, adhesive tape or the like as described, but their positional establishment is by no means limited to these positions or methods. In the case of a horse the sensor might be established between the upper surface of horseshoe 44 and horse hoof 45. This positioning provides greater protection for the sensor than if it be positioned on the bottom surface of a horseshoe but the positioning is less convenient as the horseshoe must be removed or loosened to accomplish positioning or removal of the sensor. Similarly some special channel or chamber may be provided in a shoe structure associated with an animal foot, or possibly in the foot itself in the case of a hoofed animal, to receive and maintain the sensor of my invention. In the case of human feet the sensor might quite conveniently be incorporated within a shoe structure in a position between the foot of a user and the ultimate surface supporting the foot as well as on the lower surface of the foot itself.

It should be noted from the foregoing description that my invention is not necessarily limited to use with animal feet, but might well be used in other applications to determine pressures between a multitude of separable surfaces which bear upon each other so long as the sensing element of my invention be positionally maintained between the bearing area of such surfaces at the point where such pressure is to be determined.

It should be further noted that in using my invention only extremely low voltage passes from my sensing device and through the connecting circuitry so that such electrical current might do no harm to an animal upon which the sensor is used.

It should be further noted that the fastening of my device upon an animal, and particularly on the undersurface of its feet, may be appropriately regulated to the permanency desired from a one time measurement to measurements over a period of time.

The foregoing description of my invention is necessarily of a detailed nature so that a specific embodiment of it might be set forth, but it is to be understood that various modifications of detail, rearrangement and multiplication of parts might be resorted to without departing from its spirit, essence or scope.

Having thusly described my invention, what I desire to protect by Letters Patent, and what I claim is:

1. A piezoelectric sensor for measuring the pressure between a part of an animal's foot and a reactive surface, comprising, in combination:

a flat, sheet-like plastic type, piezoelectric sensing element defining a sensing body and an elongate connecting tail with opposed sensing surfaces defined only in the medial portion of the sensing body and being completely surrounded by a peripheral non-sensing band, electrical connecting circuitry communicating with the sensor including two similar sheet-like, electrically conductive metallic foil connectors each smaller than and of shape similar to the sensor and each defining a sensor connecting portion with a connecting tail projecting therefrom, one connector communicating with the sensing surface on each side of the sensor and each connector having its tail portion positionally adhered by electrically non-conductive adhesive on the medial part of the connecting tail of the sensor, connecting wires electrically communicating with the outer end portion of each connector tail, and an electrically conductive adhesive, joining adjacent surfaces of each metallic foil connector and sensing surface, and a casement covering at least the sensor and foil connectors of the connecting circuitry, the potentially exposed surface of the casement, outwardly adjacent the sensing area, being covered by a semi-rigid protective plate of substantially the same areal extent as the sensing body of the casement.

2. A piezoelectric sensor for measuring the pressure between a part of an animal's foot and a reactive surface, comprising, in combination:

a flat, sheet-like plastic type, piezoelectric sensing element defining a sensing body and an elongate connecting tail with opposed sensing surfaces defined only in the medial portion of the sensing body and being completely surrounded by a peripheral non-sensing band, electrical connecting circuitry communicating with the sensor including two similar sheet-like, electrically conductive metallic foil connectors each smaller than and of shape similar to the sensor and each defining a sensor connecting portion with a connecting tail projecting therefrom, one connector communicating with the sensing surface on each side of the sensor and each connector having its tail portion positionally adhered by electrically non-conductive adhesive on the medial part of the connecting tail of the sensor, connecting wires electrically communicating with the outer end portion of each connector tail, and an electrically conductive adhesive joining adjacent surfaces of each metallic foil connector and sensing surface, and a casement covering at least the sensor and foil connectors of the connecting circuitry, the potentially exposed surface of the casement, outwardly adjacent the sensing area, being covered by a semi-rigid protective plate of substantially the same areal extent as the sensing body of the casement, at least the sensing part of the said casement positioned on the lowermost surface of a semi-rigid backing block, said backing block carried by and conformably fitting upon the undersurface of a horseshoe and having a flat lowermost surface extending downwardly a spaced distance from the supporting horseshoe.

* * * * *